United States Patent
Delaney et al.

(10) Patent No.: US 11,998,273 B2
(45) Date of Patent: Jun. 4, 2024

(54) INFLUENCING PUPIL DIAMETER TO IMPROVE VISION

(71) Applicant: Lenovo (Singapore) Pte. Ltd., Singapore (SG)

(72) Inventors: Mark Patrick Delaney, Raleigh, NC (US); Brett Ward, Raleigh, NC (US); John Carl Mese, Cary, NC (US); Nathan J. Peterson, Oxford, NC (US); Russell Speight VanBlon, Raleigh, NC (US); Arnold S. Weksler, Raleigh, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 446 days.

(21) Appl. No.: 17/188,786

(22) Filed: Mar. 1, 2021

(65) Prior Publication Data
US 2022/0273171 A1    Sep. 1, 2022

(51) Int. Cl.
*A61B 3/11* (2006.01)
*A61B 3/00* (2006.01)

(52) U.S. Cl.
CPC ............ *A61B 3/112* (2013.01); *A61B 3/0008* (2013.01); *A61B 3/0041* (2013.01)

(58) Field of Classification Search
CPC ........ A61B 3/112; A61B 3/008; A61B 3/0041
USPC ......................................................... 359/221
See application file for complete search history.

(56) References Cited

U.S. PATENT DOCUMENTS

| | | | |
|---|---|---|---|
| 6,417,894 B1 * | 7/2002 | Goff .................. | G02B 7/023 348/832 |
| 2004/0105075 A1 * | 6/2004 | Kandel ............... | A61B 3/063 351/221 |
| 2008/0068561 A1 * | 3/2008 | Kandel ............... | A61B 3/063 351/221 |
| 2012/0008091 A1 * | 1/2012 | Stewart .............. | A61B 3/063 351/246 |
| 2018/0333092 A1 * | 11/2018 | Roshan ............... | A61B 3/0091 |

* cited by examiner

*Primary Examiner* — Sharrief I Broome
(74) *Attorney, Agent, or Firm* — Schwegman Lundberg & Woessner, P.A.

(57) ABSTRACT

A computer device implemented method includes displaying, via the computer device, content on a display device, sensing a pupil size of a user of the computer, and adjusting a luminosity setting of the display device based on the sensed pupil size and a pupil size setpoint.

19 Claims, 4 Drawing Sheets

200 ⟶

| DIFFERENCE (210) | INCREMENT (220) |
|---|---|
| 7 | 10 |
| 6 | 10 |
| 5 | 10 |
| 4 | 10 |
| 3 | 10 |
| 2 | 5 |
| 1 | 5 |
| .8 | 1 |
| .6 | 1 |
| .5 | 1 |
| .4 | 1 |
| .3 | 1 |
| .2 | 1 |
| .1 | 0 |
| 0 | 0 |
| -.1 | 0 |
| -.2 | 1 |
| -.3 | 1 |
| -.4 | 1 |
| -.5 | 1 |
| -.6 | 1 |
| -.8 | 1 |
| -1 | 5 |
| -2 | 5 |
| -3 | 10 |
| -4 | 10 |
| -5 | 10 |
| -6 | 10 |
| -7 | 10 |

FIG. 2

INFLUENCING PUPIL DIAMETER TO IMPROVE VISION

BACKGROUND

Many devices with displays have mechanisms to adjust the brightness of the display for comfort of the user. In dark environments, users may desire the display to be less bright than in environments with bright ambient light. Users can manually adjust the brightness of the display by pressing buttons on the display or otherwise adjusting settings via a user interface.

Some devices change the brightness of their display by sensing ambient light and switching between normal and low brightness levels based on the sensed ambient light. Still further devices switch brightness levels based on time of day, with daytime brightness being brighter than nighttime brightness. Some devices even employ blue filters for nighttime viewing.

SUMMARY

A computer device implemented method includes displaying, via the computer device, content on a display device, sensing a pupil size of a user of the computer, and adjusting a luminosity setting of the display device based on the sensed pupil size and a pupil size setpoint.

BRIEF DESCRIPTION OF THE DRAWINGS

FIG. 2 is a table of display brightness increments indexed by a difference of measured pupil from a pupil size setpoint according to an example embodiment.

DETAILED DESCRIPTION

Figure 1:
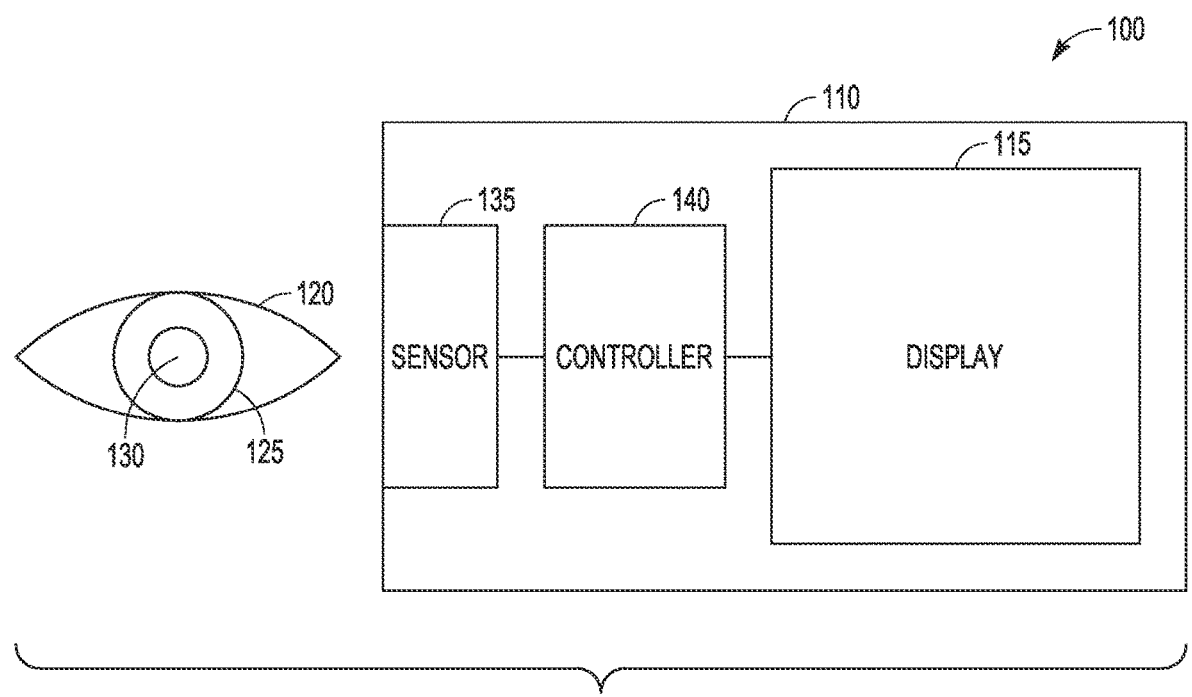
FIG. 1 is a block diagram of a system for adjusting display luminosity as a function of pupil size according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system." and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

Pupil diameter in a healthy adult can range from 2 mm to 9 mm. Vision clarity at the two extremes (close to 2 mm or greater than 5 mm) is reduced and can cause eye strain. The human body alters the size of the pupil based on the light characteristics of what is being viewed but might require some assistance. For example, in a dark setting, the pupil size might be close to 9 mm and needs additional lighting to be able to see objects more clearly. Consequently, if the pupil size is in a bright setting (pupil size is close to 2 mm), the person may be squinting to avoid the surplus light.

Many devices with displays have mechanisms to adjust the brightness of the display in response to ambient light conditions or time of day. While such adjustments may be made in an attempt to help with user comfort, user perceived clarity of displayed content may be reduced.

In various embodiments of the present inventive subject matter, a computer implemented method controls the brightness of a device display in response to sensed user pupil size.

The control is performed such that an ideal or specified user pupil size results, making displayed content better perceivable by the user. The display may be a sight glass or other device display such as a laptop display, smart phone display, tablet display, or any other electronic device display.

A large pupil lets more light in and a smaller pupil lets less light in. The body adjusts the pupil diameter relative to its surroundings or what the user is looking at to improve vision. By sensing the size of the user's pupil in real time and adjusting the brightness of the display, measured in lux, luminance, luminosity, or other measure of brightness, the user's body will correspondingly adjust the size of the pupil. Lux is the system international derived unit of illuminance, measuring luminous flux per unit area. It is equal to one lumen per square meter. Controlling the pupil size to a setpoint value between 3.0 mm to 4.0 mm provides for optimal vision and hence clarity of information or other content being displayed.

In one example, a user may be reading a document or looking at a spreadsheet. The brightness of the display is fairly constant. Once the brightness is adjusted to cause the pupil of the user to be at or near a setpoint, such as 4.0 mm, the user's pupil is at an optimal size for viewing the the display.

In another example, a healthcare worker, Chris, may be holding an otoscope to his eye to view the inside a patient's ear. A sight glass of the otoscope measure's the size of Chris' pupil to be 2 mm. The sight glass modifies the lux in a sight glass lens enabling the pupil to relax and widen. When the pupil reaches 4 mm or the optimal diameter specific to Chris, the luminosity level stabilizes. Chris is now utilizing his optimal pupil diameter to examine the patient. In essence, pupil size control is being performed by varying display brightness.

FIG. 1 is a block diagram of a luminosity control system 100. System 100 includes a device 110 having a display 115. A user's eye is shown at 120 with an iris 125 and pupil 130. The diameter of a human iris 125 varies from 10-13 mm. Pupil 130 diameter in a healthy adult can range from 2 mm to 9 mm.

Device 110 includes or is coupled to a pupil size sensor 135, such as a camera or other device that can measure pupil size. A controller 140 is coupled to receive sensor 135 generated signals, such as images, from which pupil size is determined. The images may be processed by the sensor 135 or by the controller 140 to determine a current pupil size.

The determination of current pupil size may be performed in many different ways. The iris of a user does not change over time. Thus, a calibration may be performed from a known distance by using image processing to identify the pupil and the iris, and then determine their respective diameters. Following the calibration, an image from any distance at which the pupil and iris are sufficiently distinguishable may be used to determine the pupil diameter as a proportion of size to the iris size.

An alternative sensor may simply make a rough assumption of the size of the iris as being average, 11.5 mm, and then determine pupil size based on that assumption. A user could also obtain an independent measurement of iris size and provide that measurement for use in determining pupil size.

A further alternative sensor may utilize a laser generated spot that has the same size regardless of distance. The spot may be used as a reference when projected near the eye or eyes. One or both pupils of a user may be measured. If both pupils differ in size, an average may be used, or the user may specify which pupil, left or right, to use. For example, the pupil of a known dominant eye may be specified by the user. Distance sensors may also be used to provide a distance measurement to the pupil, from which the size of the pupil may also be calculated based on the pixels corresponding to the pupil.

Proportional, integral, derivative control may be performed based on the determined current pupil size to adjust the brightness of the display 115.

In one embodiment, the control may be performed periodically based on a table of brightness increments. In other words, given a desired or setpoint pupil size of 4.0 mm, a larger measured pupil size will increment the brightness in the positive direction, making the displayed content brighter. The difference in measured size from the setpoint may be used to index into a table of increments. Increments associated with smaller differences in measured size from the setpoint may be smaller than increments associated with larger differences, such that smaller changes occur and a steady state is reached for displayed content having a steady brightness. To allow for the pupil size to react to the change, the period, or time between measurements, may be 1 second or more.

If multiple users are viewing content being displayed, the pupil size of the closest user may be used to control display brightness. Alternatively, an average of detectible pupil sizes may be used. In still further embodiments, the control may be performed in response to the attention of the user being detected as on the display. Thus, the size of the pupil or pupils of a user looking away from the display will not be used to control the display brightness. The attention of the user can be determined from roundness measures of the pupil in the captured images of the pupil. Roundness within a certain threshold signifies the user is looking at the display. The pupil and iris of a user looking away may not be detectable, or may appear oval shaped. There are many other methods of determining direction of gaze that may be used in further embodiments for determining whether or not to control the brightness at any particular point in time.

FIG. 2 is an example table 200 of brightness increments 210 indexed by the difference 220 of the measured pupil size from the setpoint pupil size. The size is expressed as the diameter of the pupil in millimeters for ease of illustration. Brightness increments are expressed in terms of a linear brightness scale of 1 to 100, with 1 being the lowest luminance and 100 being the highest luminance, or highest brightness setting. The table is just an example and may be modified in further embodiments based on empirical data.

Given that the human pupil can vary between 2 mm and 9 mm, the largest difference 220 is +7 mm and the smallest difference is −7 mm in table 200. For a difference of +7 mm to +3 mm, the brightness is increased by an increment of 10. For a different of +2 mm to +1 mm, the brightness is increased by an increment of 5. For differences of less than +1 mm, the brightness is increased by an increment of 1. For differences of less than 0.2 m, the brightness is not increased. For corresponding negative differences, the brightness is decreased by corresponding decrements, but not decreased for differences of greater than 0.2 mm. The difference may be rounded to the nearest difference listed in table 200. Table 200 may be implemented in code in further embodiments, or algorithmically to converge quickly.

The increments and decrements may be determined by experimentation in further embodiments to ensure a desired speed of achieving steady state, and minimal oscillation about the setpoint. The table as illustrated is symmetric about zero difference. Only one side need be used, with the sign of the difference simply being used to determine whether to increment or decrement the brightness.

Different pupil sized based display brightness control algorithms may be used for different types of content. For instance, if a movie is playing, or other content for which the content brightness normally changes during or between scenes, it may not be desirable to control the pupil size in real time. In such cases, pupil size control may be turned off. Alternatively, an average luminosity of the content to be displayed may be used to control pupil size, with brightness levels set accordingly. Initial calibration of the display device prior to displaying the content may be performed by displaying steady state content at the average luminosity and then adjusting the brightness to the pupil size setpoint. The brightness may then remain at that point for the duration of the playing of the content.

In a further embodiment, an average of pupil size over time, such as 10 seconds, 30 seconds, 1 minute, or 5 minutes may be used to adjust brightness while displaying content having variable brightness over time.

Figure 3:
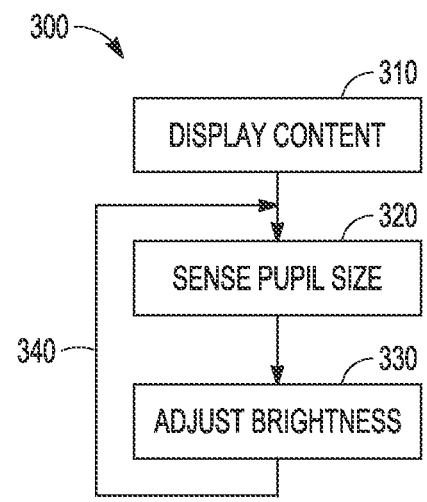
FIG. 3 is a flowchart illustrating a computer implemented method of controlling display brightness based on measured user pupil size according to an example embodiment.

FIG. 3 is flowchart illustrating a computer implemented method 300 of controlling display brightness based on measured user pupil size. At operation 310, method 300 displays content on the display device. A pupil size of the user of the computer is sensed at operation 320. At operation 330, a luminosity setting of the display device is adjusted based on the sensed pupil size and a pupil size setpoint. Adjusting the luminosity includes calculating an adjustment as a function of the pupil size. Sensing the pupil size 320 and adjusting the luminosity setting 330 is performed iteratively as illustrated by line 340, returning to operation 320. The iterations may be performed periodically, such as every second or so.

In one example, the pupil size setpoint has a value between 3.0 mm to 4.0 mm. The pupil size setpoint has a value selectable by the user. The luminosity setting may be performed using at least one of proportional, derivative, and integral control. The type of control may be selected based on content having a steady lux level. The control may alternatively be selected based on content having a variable lux level.

The sensed pupil size may be based on an average of pupil sizes of multiple users viewing content being displayed.

Figure 4:
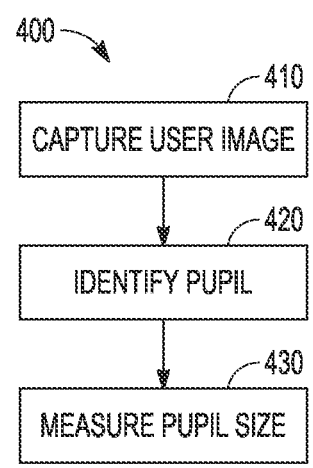
FIG. 4 is a flowchart illustrating a computer implemented method of sensing a pupil size according to an example embodiment.

FIG. 4 is a flowchart illustrating a computer implemented method 400 of sensing a pupil size. Method 400 includes operation 410 to capture an image of the user via a computer device camera. At operation 420, a pupil of the user is identified from the captured image. The size of the identified pupil is measured at operation 430. The measured value provided by method 400 may be in mm or other form suitable for control of the display brightness.

Figure 5:
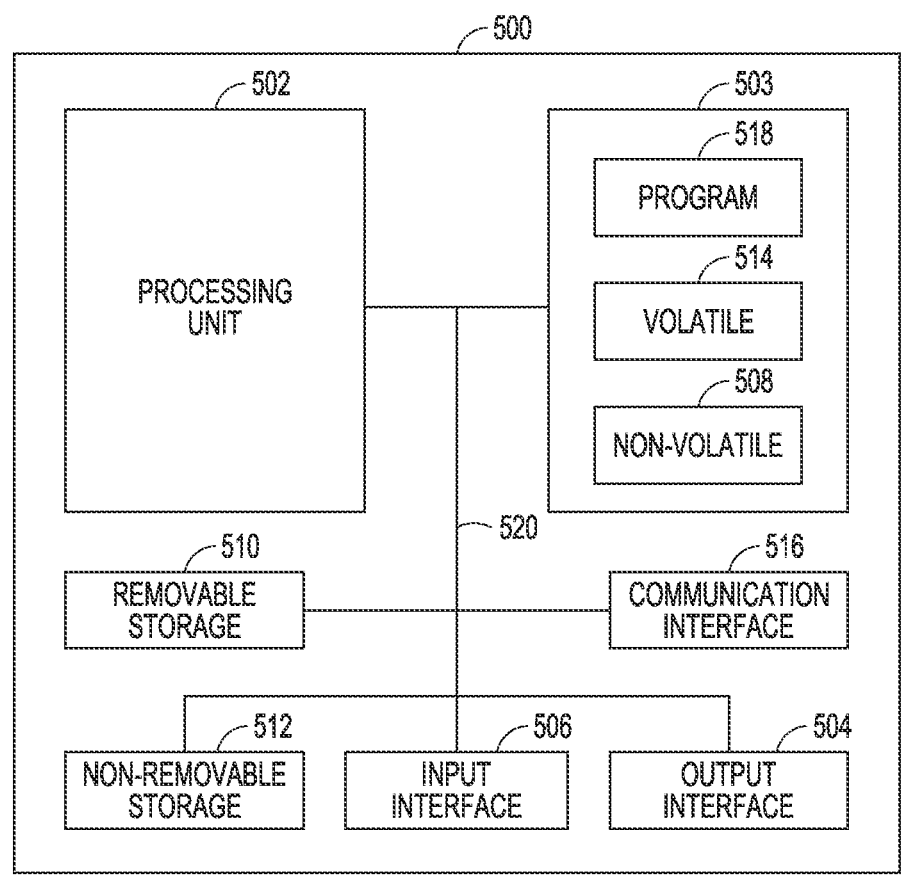
FIG. 5 is a block schematic diagram of a computer system to implement one or more example embodiments.

FIG. 5 is a block schematic diagram of a computer system 500 to adjust display brightness based on pupil size and for performing methods and algorithms according to example embodiments. All components need not be used in various embodiments.

One example computing device in the form of a computer 500 may include a processing unit 502, memory 503, removable storage 510, and non-removable storage 512. Although the example computing device is illustrated and described as computer 500, the computing device may be in different forms in different embodiments. For example, the computing device may instead be a smartphone, a tablet, smartwatch, smart storage device (SSD), or other computing device including the same or similar elements as illustrated and described with regard to FIG. 5. Devices, such as smartphones, tablets, and smartwatches, are generally collectively referred to as mobile devices or user equipment.

Although the various data storage elements are illustrated as part of the computer 500, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 503 may include volatile memory 514 and non-volatile memory 508. Computer 500 may include—or have access to a computing environment that includes—a variety of computer-readable media, such as volatile memory 514 and non-volatile memory 508, removable storage 510 and non-removable storage 512. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 500 may include or have access to a computing environment that includes input interface 506, output interface 504, and a communication interface 516. Output interface 504 may include a display device, such as a touchscreen, that also may serve as an input device. The input interface 506 may include one or more of a touchscreen, touchpad, mouse, keyboard, camera, one or more device-specific buttons, one or more sensors integrated within or coupled via wired or wireless data connections to the computer 500, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 500 are connected with a system bus 520.

Computer-readable instructions stored on a computer-readable medium are executable by the processing unit 502 of the computer 500, such as a program 518. The program 518 in some embodiments comprises software to implement one or more methods described herein. A hard drive. CD-ROM, and RAM are some examples of articles including a non-transitory computer-readable medium such as a storage device. The terms computer-readable medium, machine readable medium, and storage device do not include carrier waves to the extent carrier waves are deemed too transitory. Storage can also include networked storage, such as a storage area network (SAN). Computer program 518 along with the workspace manager 522 may be used to cause processing unit 502 to perform one or more methods or algorithms described herein.

Examples

1. A computer device implemented method includes displaying, via the computer device, content on a display device, sensing a pupil size of a user of the computer, and adjusting a luminosity setting of the display device based on the sensed pupil size and a pupil size setpoint.

2. The method of example 1 wherein sensing the pupil size and adjusting the luminosity setting is performed iteratively.

3. The method of any of examples 1-2 wherein sensing the pupil size and adjusting the luminosity setting is performed periodically.

4. The method of any of examples 1-3 wherein the pupil size setpoint has a value between 3.0 mm to 4.0 mm.

5. The method of any of examples 1-4 wherein the pupil size setpoint has a value selectable by the user.

6. The method of any of examples 1-5 wherein adjusting the luminosity setting is performed using at least one of proportional, derivative, and integral control.

7. The method of example 6 wherein the control is selected based on content having a steady lux level.

8. The method of example 6 wherein the control is selected based on content having a variable lux level.

9. The method of any of examples 1-8 wherein the sensed pupil size is based on an average of pupil sizes of multiple users.

10. The method of any of examples 1-9 wherein sensing the pupil size includes capturing an image of the user via a computer device camera, identifying a pupil of the user, and measuring the size of the identified pupil.

11. A machine-readable storage device has instructions for execution by a processor of a machine to cause the processor to perform operations to perform a method. The operations include displaying, via the computer device, content on a display device, sensing a pupil size of a user of the computer, and adjusting a luminosity setting of the display device based on the sensed pupil size and a pupil size setpoint.

12. The device of example 11 wherein sensing the pupil size and adjusting the luminosity setting is performed periodically.

13. The device of any of examples 11-12 wherein the pupil size setpoint has a value between 3.0 mm to 4.0 mm.

14. The device of any of examples 11-13 wherein adjusting the luminosity setting is performed using at least one of proportional, derivative, and integral control.

15. The device of example 14 wherein the control is selected based on content having a steady lux level.

16. The device of example 14 wherein the control is selected based on content having a variable lux level.

17. The device of any of examples 11-16 wherein the sensed pupil size is based on an average of pupil sizes of multiple users.

18. The device of any of examples 11-17 wherein operations for sensing the pupil size include capturing an image of the user via a computer device camera, identifying a pupil of the user, and measuring the size of the identified pupil.

19. A device includes a processor and a memory device coupled to the processor and having a program stored thereon for execution by the processor to perform operations. The operations include displaying, via the computer device, content on a display device, sensing a pupil size of a user of the computer, and adjusting a luminosity setting of the display device based on the sensed pupil size and a pupil size setpoint.

20. The device of example 19 wherein sensing the pupil size and adjusting the luminosity setting is performed periodically and wherein the pupil size setpoint has a value between 3.0 mm to 4.0 mm.

21. The device of any of examples 19-20 wherein the sensed pupil size is based on an average of pupil sizes of multiple users.

22. The device of example 19-21 wherein sensing the pupil size is performed by operations including capturing an image of the user via a computer device camera, identifying a pupil of the user, and measuring the size of the identified pupil.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A computer device implemented method comprising:
   displaying, via the computer device, content on a display device;
   sensing a pupil size of a user of the computer viewing the content by:
      capturing an image of the user via a computer device camera;
      identifying a pupil of the user in the image; and
      measuring the size of the identified pupil; and
   adjusting a luminosity setting of the display device based on the sensed pupil size and a pupil size setpoint to control the pupil size to the pupil size setpoint.

2. The method of claim 1 wherein sensing the pupil size and adjusting the luminosity setting is performed iteratively.

3. The method of claim 1 wherein sensing the pupil size and adjusting the luminosity setting is performed periodically.

4. The method of claim 1 wherein the pupil size setpoint has a value between 3.0 mm to 4.0 mm.

5. The method of claim 1 wherein the pupil size setpoint has a value selectable by the user.

6. The method of claim 1 wherein adjusting the luminosity setting is performed using at least one of proportional, derivative, and integral control.

7. The method of claim 6 wherein the control is selected based on content having a steady lux level.

8. The method of claim 6 wherein the control is selected based on content having a variable lux level.

9. The method of claim 1 wherein the sensed pupil size is based on an average of pupil sizes of multiple users.

10. A machine-readable storage device having instructions for execution by a processor of a machine to cause the processor to perform operations to perform a method, the operations comprising:
    displaying, via the computer device, content on a display device;
    sensing a pupil size of a user of the computer viewing the display device; and
    adjusting a luminosity setting of the display device based on the sensed pupil size and a pupil size setpoint to control the pupil size.

11. The device of claim 10 wherein sensing the pupil size and adjusting the luminosity setting is performed periodically and wherein the pupil size setpoint has a value between 3.0 mm to 4.0 mm.

12. The device of claim 10 wherein adjusting the luminosity setting is performed using at least one of proportional, derivative, and integral control.

13. The device of claim 12 wherein the control is selected based on content having a steady lux level or is selected based on content having a variable lux level.

14. The device of claim 10 wherein the sensed pupil size is based on an average of pupil sizes of multiple users.

15. The device of claim 10 wherein operations for sensing the pupil size comprise:
- capturing an image of the user via a computer device camera;
- identifying a pupil of the user; and
- measuring the size of the identified pupil.

16. A device comprising:
- a processor; and
- a memory device coupled to the processor and having a program stored thereon for execution by the processor to perform operations comprising:
    - displaying, via the computer device, content on a display device;
    - sensing a pupil size of a user of the computer; and
    - adjusting a luminosity setting of the display device based on the sensed pupil size and a pupil size setpoint to control the pupil size.

17. The device of claim 16 wherein sensing the pupil size and adjusting the luminosity setting is performed periodically and wherein the pupil size setpoint has a value between 3.0 mm to 4.0 mm.

18. The device of claim 16 wherein the sensed pupil size is based on an average of pupil sizes of multiple users.

19. The device of claim 16 wherein sensing the pupil size is performed by operations comprising:
- capturing an image of the user via a computer device camera;
- identifying a pupil of the user; and
- measuring the size of the identified pupil.

* * * * *